US00PP11584P

United States Patent [19]

Griffith, Jr.

[11] Patent Number: Plant 11,584

[45] Date of Patent: Oct. 17, 2000

[54] COLEUS PLANT NAMED 'RADIANCE'

[75] Inventor: George W. Griffith, Jr., Gainesville, Fla.

[73] Assignee: Hatchett Creek Farms, Inc., Gainesville, Fla.

[21] Appl. No.: 09/221,612

[22] Filed: Dec. 28, 1998

[51] Int. Cl.[7] ..... A01H 5/00

[52] U.S. Cl. ..... Plt./373

[58] Field of Search ..... Plt./373, 263

*Primary Examiner*—Howard J. Locker
*Assistant Examiner*—Kent L. Bell
*Attorney, Agent, or Firm*—C. A. Whealy

[57] ABSTRACT

A distinct cultivar of Coleus plant named 'Radiance', characterized by its upright and somewhat outwardly spreading plant habit; multi-colored leaves with green, yellow-green to white, red-purple and deep maroon areas of varying size and shape depending on light levels; lack of flower development; excellent garden performance and tolerance to high temperatures and full sun conditions.

1 Drawing Sheet

BACKGROUND OF THE INVENTION

The present invention relates to a new and distinct cultivar of Coleus plant, botanically known as *Coleus×hybridus*, and hereinafter referred to by the cultivar name 'Radiance'. The new Coleus is marketed under the trade name Solar Radiance.

The new Coleus was discovered by the Inventor in Gainesville, Fla. as a naturally-occurring lateral branch mutation of a plant of the nonpatented *Coleus×hybridus* cultivar 'Solar Sunrise' in 1996.

Asexual reproduction of the new cultivar by terminal and stem cuttings taken at Gainesville, Fla., has shown that the unique features of this new Coleus are stable and reproduced true to type in successive generations.

SUMMARY OF THE INVENTION

Plants of the cultivar 'Radiance' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Radiance'. These characteristics in combination distinguish 'Radiance' as a new and distinct cultivar:

1. Upright and somewhat outwardly spreading plant habit.

2. Multi-colored leaves with green, yellow-green to white, red-purple and deep maroon areas of varying size and shape depending on light levels.

3. Lack of flower development.

4. Excellent garden performance; tolerant to high temperatures and full sun conditions.

5. Less susceptible to bacterial pathogens common to Coleus.

Plants of the cultivar 'Radiance' can be compared to plants of the parent cultivar, the nonpatented *Coleus×hybridus* cultivar 'Solar Sunrise'. Leaves of plants of the new Coleus are green, yellow-green to white, red-purple and deep maroon whereas leaves of plants of the parent cultivar are primarily green and maroon. In addition, in side-by-side comparisons conducted in Gainesville, Fla., plants of the new Coleus were more compact and had smaller leaves than plants of the parent cultivar.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of the new Coleus grown in a one-liter container under outdoor cultivation. Foliage colors in the photograph may appear lighter than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown in one-liter containers under outdoor production conditions during the summer and autumn in Gainesville, Fla., and Keller, Tex.

Botanical classification: *Coleus×hybridus* cultivar 'Radiance'.

Parentage: Naturally-occurring branch mutation of *Coleus×hybridus* cultivar 'Solar Sunrise', not patented.

Propagation:

- *Type cutting.*—Terminal and stem cuttings.
- *Time to initiate roots.*—Summer: About 4 days at temperatures of about 29° C. Winter: About 4 days at temperatures of about 21° C.
- *Time to develop roots.*—Summer: About 21 days at temperatures of about 35° C. Winter: About 28 days at temperatures of about 24° C.
- *Rooting habit.*—Numerous and fine.

Plant description:

- *Type.*—Annual succulent herb in temperate regions; may be perennial in subtropical and tropical regions. Typically grown as container or garden plants.
- *Crop time.*—From cuttings, about 10 weeks are required to produce a fully-grown finished plant in a one-liter container.
- *Form.*—Upright and somewhat outwardly spreading. Appropriate for one-liter containers.
- *Branching habit.*—Although freely branching, pinching (removal of apices) will enhance branching; lateral branches may potentially form at every node.
- *Plant height (from soil level to top of plant plane.*—About 52 cm.
- *Area of spread.*—About 41 cm.
- *Vigor.*—Vigorous, rapid.

*Branches*.—Diameter: About 6.5 mm. Internode length: About 4.2 cm. Shape: Square in cross-section. Strength: Strong. Texture: Very minute hairs. Color: Very dark maroon, darker than 187A.

*Foliage description*.—Leaves simple, generally symmetrical, opposite and long persisting. Length: About 9.7 cm. Width: About 7.4 cm. Aspect: Mostly horizontal. Shape: Ovate. Apex: Acute. Base: Obtuse. Margin: Crenate. Texture: Pubescent on both surfaces, veins prominent on lower surface. Color: Multi-colored, base of leaf, typically green to yellow green to white; center of leaf to apex, deep maroon, or red-purple; margin, green. Actual patterns and relative colored areas depend on light level. With increasing light level, red colored areas are more dominant. Various spots and splashes of the different colors appear randomly throughout the leaf predominantly along lateral veins. Young foliage, upper surface: Center towards base, green, 144A; center towards apex, deep maroon, 187A; margin, green, 144A; various spots and splashes of green and deep maroon throughout the leaf; venation, 187A. Young foliage, lower surface: Green, close to 146C; venation, 187A. Mature foliage, upper surface: Center towards base, green, 144A, to yellow green, 154A, to white, 155A; center towards apex, deep maroon, 187A; center and radiating along veins, red-purple, 61A; margin, green, 144A; various spots and splashes of green and deep maroon throughout the leaf; venation, 187A. Mature foliage, lower surface: Green, close to 146C; random yellow green, 154A, white, 155A, and/or deep maroon, 187A, spots; venation, deep maroon, 187A, towards base and light whitish green towards apex. Petiole: Length: About 3.5 cm. Diameter: About 2.5 mm. Color: Close to 187A.

Flower description: Flowers have not been observed to date on plants of the new Coleus.

Weather tolerance: Plants of the new Coleus have exhibited good tolerance to high temperatures and full sun conditions; excellent garden performance.

Disease resistance: Under commercial conditions, plants of the new Coleus are less susceptible to bacterial diseases common to Coleus.

It is claimed:

1. A new and distinct cultivar of Coleus plant named 'Radiance', as illustrated and described.

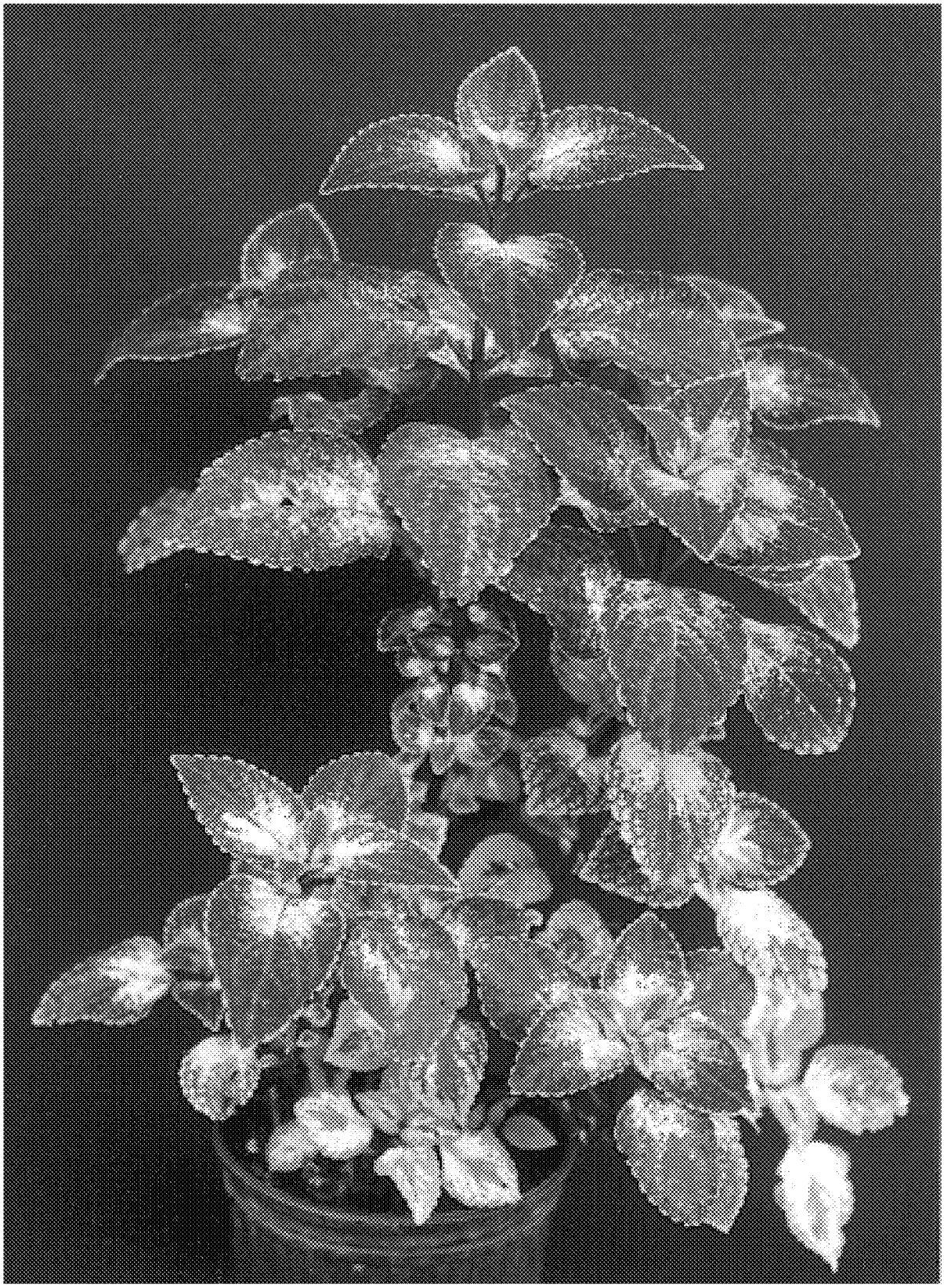

* * * * *